United States Patent
Wang et al.

(10) Patent No.: US 8,159,665 B2
(45) Date of Patent: Apr. 17, 2012

(54) APPARATUS AND METHODS FOR FLUORESCENCE SUBTRACTION IN RAMAN SPECTROSCOPY

(75) Inventors: Sean Xiaolu Wang, Wilmington, DE (US); Qun Li, Newark, DE (US)

(73) Assignee: BWT Property, Inc., Newark, DE (US)

(*) Notice: Subject to any disclaimer, the term of this patent is extended or adjusted under 35 U.S.C. 154(b) by 0 days.

(21) Appl. No.: 12/840,381

(22) Filed: Jul. 21, 2010

(65) Prior Publication Data

US 2012/0019818 A1   Jan. 26, 2012

(51) Int. Cl.
*G01J 3/44* (2006.01)
(52) U.S. Cl. ....................................................... 356/301
(58) Field of Classification Search .................. 356/301, 356/72–73
See application file for complete search history.

(56) References Cited

U.S. PATENT DOCUMENTS

| | | | |
|---|---|---|---|
| 7,145,651 B2 | 12/2006 | Li et al. | |
| 2001/0034478 A1* | 10/2001 | Lambert et al. | 600/318 |
| 2004/0127778 A1* | 7/2004 | Lambert et al. | 600/318 |
| 2006/0229515 A1* | 10/2006 | Sharareh et al. | 600/476 |
| 2007/0049809 A1* | 3/2007 | Bechtel et al. | 600/316 |

* cited by examiner

*Primary Examiner* — Tarifur Chowdhury
*Assistant Examiner* — Abdullahi Nur

(57) ABSTRACT

An improved apparatus and method for fluorescence subtraction in Raman spectroscopy, where a narrow band light source and a broad band light source are utilized to stimulate Raman scattering and fluorescence emission from the same subject to produce two Raman/fluorescence spectra. The two light sources, with matched output power, produce similar level of fluorescence emission, yet the Raman scattering signal produced by the broad band light source has much lower spectral intensity than that produced by the narrow band light source. By subtracting the two Raman/fluorescence spectra, the weak Raman signal can be extracted from a strong fluorescence background.

10 Claims, 4 Drawing Sheets

APPARATUS AND METHODS FOR FLUORESCENCE SUBTRACTION IN RAMAN SPECTROSCOPY

FIELD OF THE INVENTION

This invention generally relates to Raman spectroscopy, and more specifically to apparatus and methods for fluorescence subtraction in Raman spectroscopy.

BACKGROUND

Raman spectroscopy has been demonstrated as a powerful non-invasive analytical technology for material characterization and identification. However, for some composite materials, organic compounds, and biological samples, the strong fluorescence emission that is stimulated by the excitation laser often overwhelms the weak Raman signal.

Several techniques have been proposed to suppress the interference of the fluorescent emission. In one approach as disclosed by Fujiwara M, et al. in *Applied Spectroscopy*, Vol. 40, p. 137, 1986, the wavelength of the excitation laser is shifted to near-infrared (NIR) region. However, the Raman signal also becomes weaker, since the Raman scattering cross-section is inversely proportional to the fourth power of excitation wavelength. To compensate for the weak Raman signal, a higher laser power has to be used, which may damage the subject sample. Another approach uses deep UV laser for Raman excitation as disclosed by Bowman W D, et al. in *Journal of Raman Spectroscopy*, Vol. 9, p. 369, 1980. But the lasers at this wavelength are both bulky and expensive. In addition, the UV light may be harmful and invasive to certain samples.

Other approaches employ some laser modulation techniques. For example, by taking advantage of the fact that fluorescence emission and Raman emission have different decay times, the two spectra can be separated in the time domain by stimulating the material with an ultra short pulse laser as disclosed by Howard J, et al in *Journal of Physics E: Scientific Instruments*, Vol. 19, p. 934, 1986. This approach requires the pulse width of the laser to be in the order of pico-seconds. Commonly a nonlinear Kerr gate is used to separate the fluorescence emission from the Raman signal. Another approach, which is named as 'shifted excitation Raman difference spectroscopy' (SERDS), is proposed by Shreve AP, et al. in *Applied Spectroscopy*, Vol. 46, p. 707, 1992. In this approach, two similar Raman spectra with a small shift in wavelength are obtained using a tunable laser. The difference between the two spectra is used to reconstruct the Raman spectrum. This approach utilizes the fact that the fluorescence spectra are generally insensitive to the small shift in excitation wavelength, while the Raman peaks shift exactly in unison with the excitation wavelength. A simpler but less effective approach is proposed by S. E. J. Bell, et al. in *Analyst*, Vol. 8, p. 1729, 1998, which obtains the difference Raman spectrum by shifting the position of the spectrometer, thus avoiding the use of the tunable laser. Although the above disclosed techniques achieved some success, their instrumentation complexity and cost issues prevented their wide adoption.

SUMMARY OF THE INVENTION

It is thus the goal of the present invention to provide an improved apparatus and method for fluorescence subtraction in Raman spectroscopy, where a narrow band light source, e.g. a laser, and a broad band light source, e.g. a light emitting diode (LED) or a super luminescence diode (SLD) are utilized to stimulate Raman scattering and fluorescence emission from the same subject to produce two Raman/fluorescence spectra. The two light sources, with matched output power, produce similar levels of fluorescence emission, yet the Raman scattering signal produced by the broad band light source has much lower spectral intensity than that produced by the narrow band light source. By subtracting the two Raman/fluorescence spectra, the weak Raman signal can be extracted from a strong fluorescence background.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 3 shows the application of the fluorescence subtraction method on an acetone/Rodamine 6G mixture, where FIG. 4 shows the application of the fluorescence subtraction method on an orange rind sample, where

Figure 1:
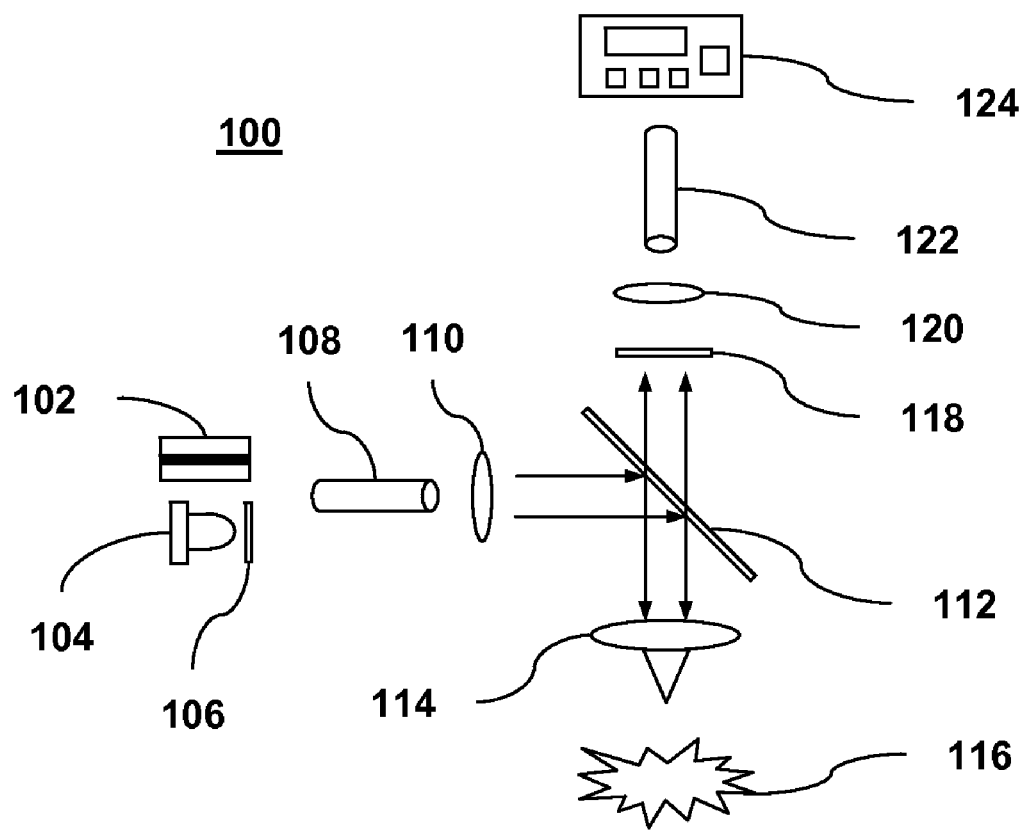
FIG. 1 illustrates an exemplary Raman spectroscopic apparatus that utilizes a broad band light source and a narrow band light source for fluorescence subtraction.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to fluorescence subtraction in Raman spectroscopy. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

A preferred embodiment of the Raman spectroscopic apparatus is shown in FIG. 1. The excitation light source of the Raman spectroscopic apparatus 100 comprises two light sources: a narrow band laser light source 102 and a broad band LED light source 104. The output spectrum of the LED light source 104 is filtered by a bandpass optical filter 106, which has a central wavelength matching with the laser wavelength. The bandwidth of the optical filter 106 is on the order of 5-20 nm (nanometer). An optical fiber 108 is employed for delivering the laser light and the LED light. The laser 102 and the LED 104 are adjusted to produce the same output power at the output end of the optical fiber 108. A first optical lens 110 collects and collimates the laser light and the LED light that is emitted from the optical fiber 108. The collimated light is then reflected by a dichroic filter 112 to a second optical lens 114. The optical lens 114 focuses the laser light and the LED light onto a sample 116 to stimulate Raman scattering as well as fluorescence emission from the sample 116. The Raman scattering and fluorescence signal is collected by the same optical lens 114 and filtered by the dichroic filter 112 for partially removing the Rayleigh scattering and the reflected laser and LED light from the sample 116. A longpass edge filter 118 following the dichroic filter 112 is used to further remove the Rayleigh scattering from the Raman scattering signal. The filtered Raman scattering and fluorescence signal is focused by a third optical lens 120 into another optical fiber 122 and delivered into a CCD (charge-coupled device) array spectrograph 124 for spectral analysis. In a slight variation of the present embodiment, the LED light source may be replaced with other types of broad band coherent or non-coherent light sources, such as super luminescence diodes (SLDs), supercontinuum light sources, and broad band fiber lasers for enhanced output power.

Figure 2:
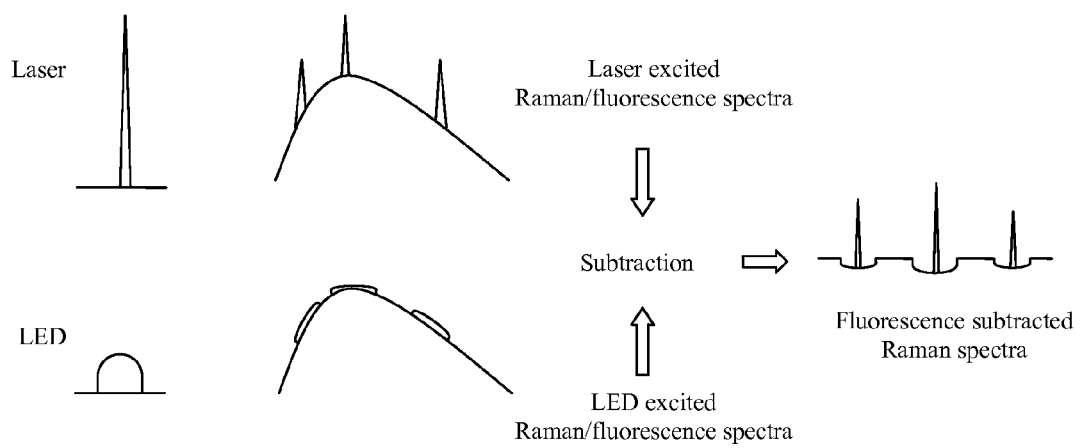
FIG. 2 illustrates the operation principle of the fluorescence subtraction method.

The operation principle of the fluorescence subtracted Raman spectroscopic method is further illustrated in FIG. 2. The laser light and the filtered LED light have the same central wavelength and output power, yet the spectral intensity (defined as output power divided by spectral bandwidth) of the laser light is over 1-2 orders of magnitude higher than that of the LED light. The laser light and the LED light produce similar level of fluorescence emission due to the following two reasons. First, the fluorescence emission is generally insensitive to small shifts in excitation wavelength since the band gap between ground state and excited state of the material is fixed. Second, the bandwidth of the fluorescence emission is generally much broader than the bandwidth of the laser light and the filtered LED light. Thus the broader bandwidth of the LED light will only contribute a slight broadening to the fluorescence spectra. In comparison, since the spectral intensity of the Raman scattering signal is proportional to the spectral intensity of the excitation light source, the Raman scattering signal excited by the laser light exhibits much higher spectral intensity than that excited by the LED light. By producing two individual Raman/fluorescence spectra with the laser and the LED light source, respectively, and performing a subtraction of the two spectra, the weak Raman signal can be extracted from a strong fluorescence background. In most cases, the LED excited Raman signal is so weak in spectral intensity such that it can be neglected. Therefore, the fluorescence subtracted Raman spectrum is nearly identical to the real Raman spectrum of the subject sample. In cases where the Raman scattering of the sample is relatively strong, the LED excited Raman signal becomes notable, which causes the baseline of the fluorescence subtracted Raman spectrum to become negative around the strong Raman peaks. This can be easily solved by mathematically reconstructing the real Raman spectrum from the fluorescence subtracted Raman spectrum.

Figure 3A:
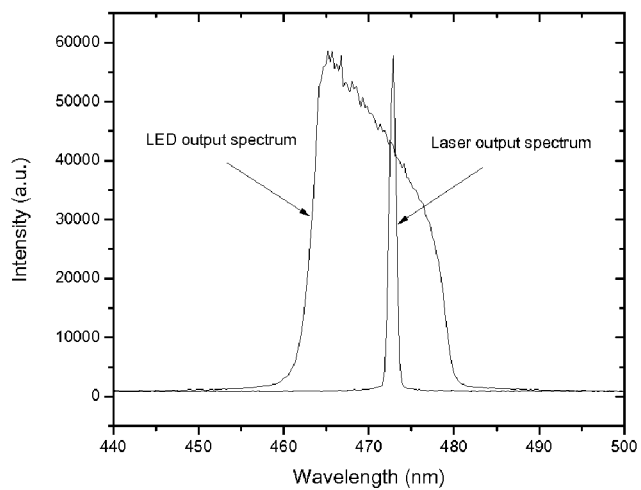
FIG. 3a shows the output spectra of the two excitation light sources (a laser and an LED)
Figure 3B:
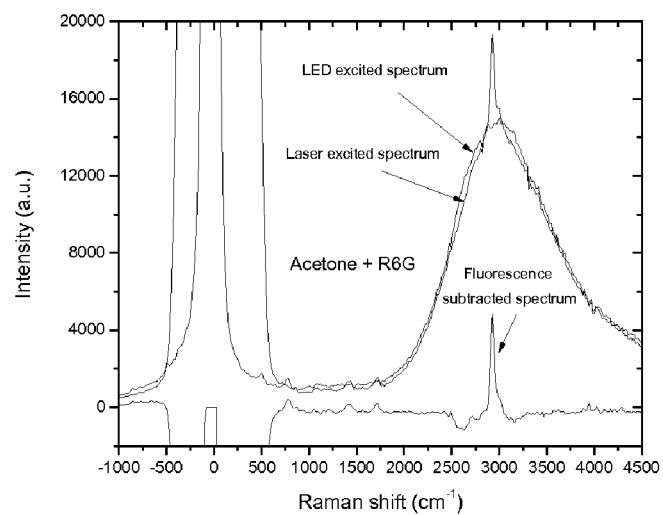
FIG. 3b shows the obtained Raman/fluorescence spectra by the laser and the LED as well as the fluorescence subtracted Raman spectra.
Figure 3C:
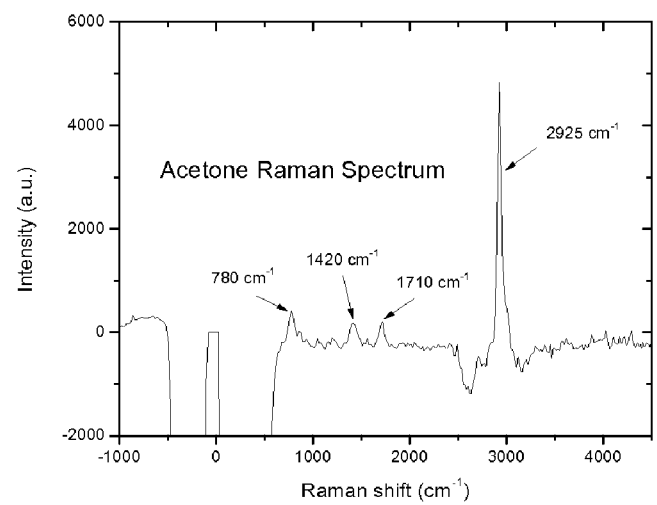
FIG. 3c shows an expanded view of the fluorescence subtracted Raman spectra.

A demonstration of the fluorescence subtraction method is shown in FIG. 3. Here the light source comprises a 473 nm diode-pumped solid state laser (DPSSL) and a high power blue LED with its output spectrum filtered by a bandpass filter centered at 473 nm. The filter has a bandwidth of around 15 nm. The sample to be measured is acetone with certain level of Rhodamine 6G dissolved in it. The output spectra of the laser and the filtered LED light sources are shown in FIG. 3a. The power of the laser light and the filtered LED light are adjusted to be both around 0.1 mW (milliwatt) on the subject sample. The laser light and the LED light produce two Raman/fluorescence spectra, respectively as shown in FIG. 3b. It can be seen that the laser excited Raman/fluorescence spectrum shows both the Raman bands of acetone and the fluorescence emission of Rhodamine 6G, while the LED excited Raman/fluorescence spectrum shows only the fluorescence emission of Rhodamine 6G. A subtraction of the two Raman/fluorescence spectra eliminates the interference of Rhodamine 6G fluorescence and reveals a clear Raman spectrum of acetone as shown in FIG. 3c.

Figure 4A:
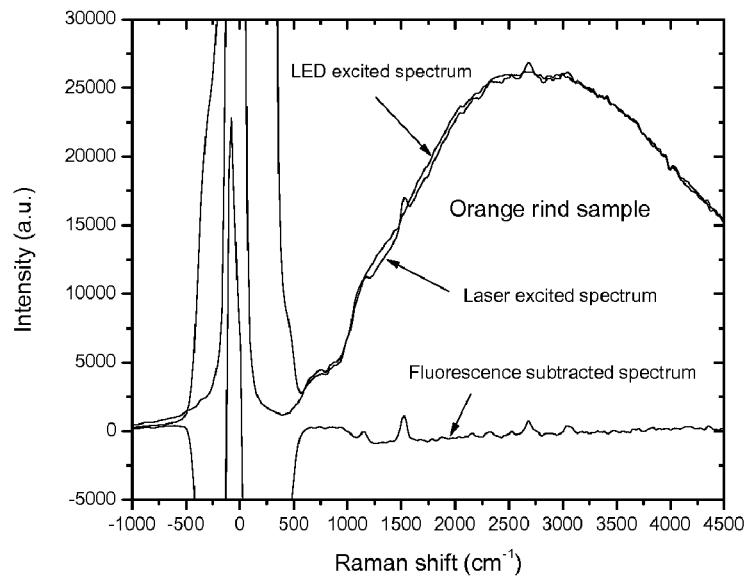
FIG. 4a shows the obtained Raman/fluorescence spectra by the laser and the LED light source as well as the fluorescence subtracted Raman spectra.
Figure 4B:
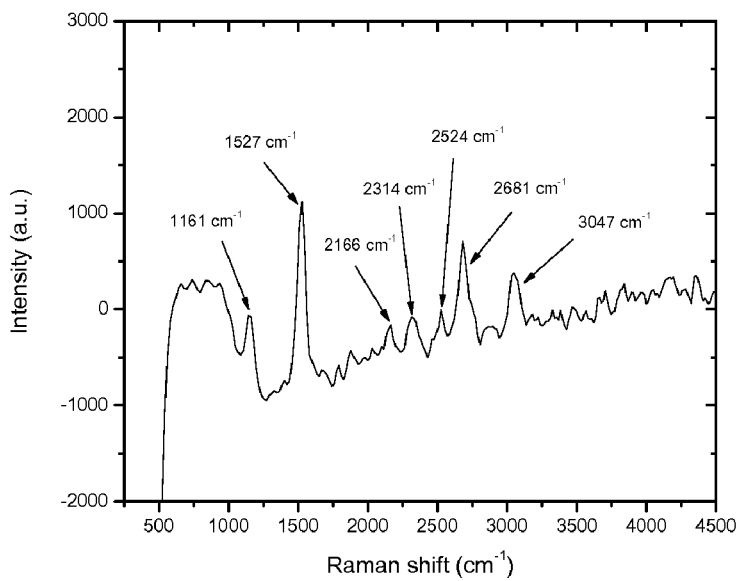
FIG. 4b shows an expanded view of the fluorescence subtracted Raman spectra.

A practical application of the fluorescence subtraction method is shown in FIG. 4, where the Raman/fluorescence spectrum of an orange rind sample is measured with both the laser light and the LED light. As shown in FIG. 4a, both the laser and the LED induced Raman/fluorescence spectra exhibit a strong fluorescence background with the laser induced Raman/fluorescence spectrum showing certain indistinctive Raman peaks. The LED induced Raman/fluorescence spectrum is subtracted from the laser induced Raman/fluorescence spectrum and the result is shown in FIG. 4b. It can be seen that the interference of the fluorescence background is greatly suppressed. Seven clearly identifiable Raman bands at 1161 $cm^{-1}$, 1527 $cm^{-1}$, 2166 $cm^{-1}$, 2314 $cm^{-1}$, 2524 $cm^{-1}$, 2681 $cm^{-1}$, and 3047 $cm^{-1}$ are revealed. The slope of the baseline in FIG. 4b is believed to be caused by the non-symmetrical spectral shape of the LED light source as shown in FIG. 3a, which can be easily solved by choosing better LED sources or by modifying the spectral response of the bandpass filter.

The fluorescence subtraction method as disclosed in the present invention offers several advantages over the SERDS approach. (i) In the SERDS approach, the shift of the excitation wavelength results in a wavelength shift of the Raman peaks. As a result, any non-uniformity in the spectral response of the spectrograph will cause a change in the detected intensity of the shifted Raman peaks. This introduces extra noise to the obtained Raman spectrum. In comparison, the laser and the LED light source in the present invention have the same output wavelength except for a bandwidth and spectral intensity difference. Thus the spectral non-uniformity of the spectrograph will not contribute extra noise. (ii) In most cases, the LED excited Raman signal is so weak in spectral intensity such that it can be neglected. Therefore, the fluorescence subtracted Raman spectrum is nearly identical to the real Raman spectrum of the subject. No further mathematical processing is required to reconstruct the Raman spectrum.

(iii) The present method does not require a tunable laser, thus reduces the instrumentation complexity and cost of the approach.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A spectroscopic apparatus for measuring the Raman scattering spectrum of a physical material that exhibits fluorescence, the spectroscopic apparatus comprising:
    a narrow band light source for stimulating a first Raman/fluorescence signal from the physical material;
    a broad band light source for stimulating a second Raman/fluorescence signal from the physical material; and
    a spectrograph for measuring said first and second Raman/fluorescence signal and obtaining a first and a second Raman/fluorescence spectrum, wherein said second Raman/fluorescence spectrum is subtracted from said first Raman/fluorescence spectrum to obtain a fluorescence subtracted Raman spectrum of the physical material.

2. The spectroscopic apparatus of claim 1, wherein said broad band light source has substantially the same output power as said narrow band light source.

3. The spectroscopic apparatus of claim 1, wherein said broad band light source has substantially the same central wavelength as said narrow band light source.

4. The spectroscopic apparatus of claim 1, wherein said narrow band light source comprises a narrow band laser light source.

5. The spectroscopic apparatus of claim 1, wherein said broad band light source comprises a light emitting diode (LED) light source.

6. The spectroscopic apparatus of claim 1, wherein said broad band light source comprises a super luminescence diode (SLD) light source.

7. The spectroscopic apparatus of claim 1, wherein said broad band light source comprises a broad band coherent light source.

8. The spectroscopic apparatus of claim 1, wherein said broad band light source comprises a broad band non-coherent light source.

9. The spectroscopic apparatus of claim 1, wherein said broad band light source is filtered by a bandpass optical filter having a central wavelength matched with the central wavelength of said narrow band light source.

10. A method for measuring the Raman spectrum of a physical material that exhibits fluorescence, the method comprising the steps of:
    providing a narrow band light source for stimulating a first Raman/fluorescence signal from the physical material;
    providing a broad band light source for stimulating a second Raman/fluorescence signal from the physical material; and
    providing a spectrograph for measuring said first and second Raman/fluorescence signal and obtaining a first and a second Raman/fluorescence spectrum, wherein said second Raman/fluorescence spectrum is subtracted from said first Raman/fluorescence spectrum to obtain a fluorescence subtracted Raman spectrum of the physical material.

* * * * *